United States Patent
Lin et al.

(10) Patent No.: US 6,527,773 B1
(45) Date of Patent: *Mar. 4, 2003

(54) CERVICAL DOWEL AND INSERTION TOOL

(75) Inventors: Ching-Yi Lin, Fort Lee, NJ (US); Jo-Wen Lin, Titon Falls, NJ (US)

(73) Assignee: Osteotech, Inc., Eatontown, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/685,530

(22) Filed: Oct. 10, 2000

Related U.S. Application Data

(60) Provisional application No. 60/158,074, filed on Oct. 7, 1999.

(51) Int. Cl.⁷ .............................................. A61B 17/56
(52) U.S. Cl. ............................. 606/61; 606/73; 606/76; 606/99; 623/16.11; 623/17.11
(58) Field of Search ................ 606/61, 76, 77, 606/73, 99, 104; 623/17.11, 17.16, 16.11; 441/403, 405, 393, 402, 407, 919, 410; D9/439; D12/197

(56) References Cited

U.S. PATENT DOCUMENTS

| | | |
|---|---|---|
| 3,486,505 A | 12/1969 | Morrison |
| 3,604,487 A * | 9/1971 | Gilbert ........................ 606/104 |
| 3,848,601 A | 11/1974 | Ma et la. |
| 4,033,244 A * | 7/1977 | Jacobson .................... 411/919 |
| 4,349,921 A | 9/1982 | Kuntz |
| 4,566,466 A | 1/1986 | Ripple et al. |
| 4,743,256 A | 5/1988 | Brantigan |
| 4,753,235 A | 6/1988 | Hasson |
| 4,877,020 A | 10/1989 | Vich |
| 4,878,915 A * | 11/1989 | Brantigan ................ 623/17.11 |
| 4,955,885 A | 9/1990 | Meyers |

(List continued on next page.)

OTHER PUBLICATIONS

Smith, MD et al., "Load–bearing Capacity of Corticocancellous Bone Grafts in the Spine" (truncated abstract), Aug. 1993, Journal of Bone & Joint Surgery, 75(8):1206–13.*
Jose M. Otero Vich, M.D., Anterior cervical interbody fusion with threaded cylindrical bone, J. Neurosurg 63:750–753, 1985.

*Primary Examiner*—David O. Reip
*Assistant Examiner*—Julian W. Woo
(74) *Attorney, Agent, or Firm*—Dilworth & Barrese, LLP

(57) ABSTRACT

A dowel insertion tool includes a T-shaped handle and a hollow sleeve which extends distally from the T-shaped handle. A shaft extends from the handle through the hollow sleeve and includes a transverse extension. A rotatable knob having an annular channel positioned to receive the transverse extension is supported adjacent the handle. A pin is secured to the knob and extends into a helical camming channel formed in the sleeve. Upon rotation of the knob, the pin moves within the camming channel to move the knob longitudinally about the sleeve. Movement of the knob effects longitudinal movement of the shaft. A support plate is secured to the distal end of the shaft. A pair of prongs are slidably secured to the plate. Each of the prongs includes an enlarged head portion which is slidably positioned within a slot formed in the plate. A guide member is secured to the distal end of the sleeve. The guide member includes a pair of guide bores dimensioned to receive a distal end of the prongs. The guide bores direct the prongs outwardly from the distal end of the hollow sleeve at an angle to the longitudinal axis of the sleeve. The prongs are dimensioned to be received in bores formed in the trailing end of a cervical dowel. Because the prongs engage the dowel at an angle, the dowel is both rotatably and longitudinally fixed to the insertion tool.

9 Claims, 15 Drawing Sheets

U.S. PATENT DOCUMENTS

| | | | |
|---|---|---|---|
| 5,192,327 A | | 3/1993 | Brantigan |
| 5,423,825 A | | 6/1995 | Levine |
| 5,443,514 A | | 8/1995 | Steffee |
| 5,593,409 A | * | 1/1997 | Michelson .................. 606/61 |
| 5,645,598 A | * | 7/1997 | Brosnahan, III ......... 623/17.11 |
| 5,707,371 A | | 1/1998 | Metz-Stavenhagen |
| 5,716,415 A | | 2/1998 | Steffee |
| 5,720,751 A | | 2/1998 | Jackson |
| 5,776,199 A | | 7/1998 | Michelson |
| 5,782,830 A | | 7/1998 | Farris |
| 5,814,084 A | * | 9/1998 | Grivas et al. ............ 623/16.11 |
| 5,860,973 A | * | 1/1999 | Michelson .................... 606/61 |
| 5,868,749 A | * | 2/1999 | Reed ........................... 606/76 |
| 5,885,300 A | | 3/1999 | Tokuhashi et al. |
| 5,941,882 A | * | 8/1999 | Jammet et la. ................ 606/73 |
| 6,045,554 A | * | 4/2000 | Grooms et al. ................ 606/76 |
| 6,066,174 A | | 5/2000 | Farris |
| 6,077,267 A | * | 6/2000 | Huene ......................... 606/73 |
| 6,083,225 A | | 7/2000 | Winslow et al. |
| 6,159,215 A | | 12/2000 | Urbahns et al. |

\* cited by examiner

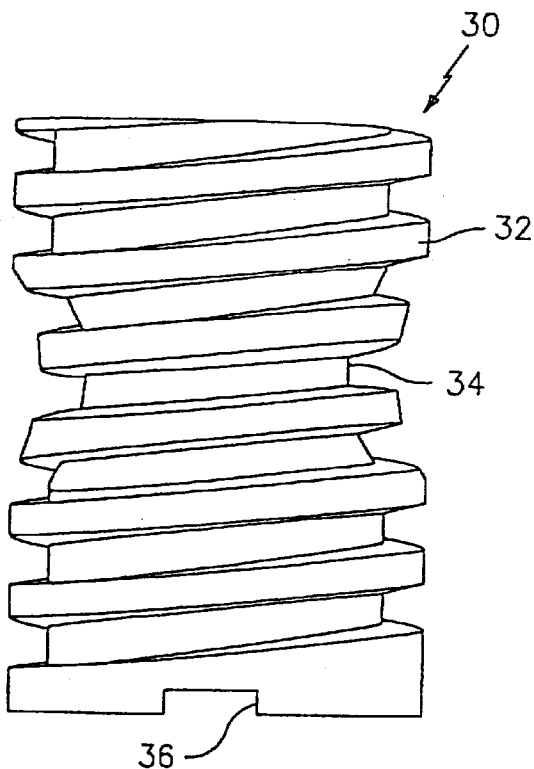
FIG. 4
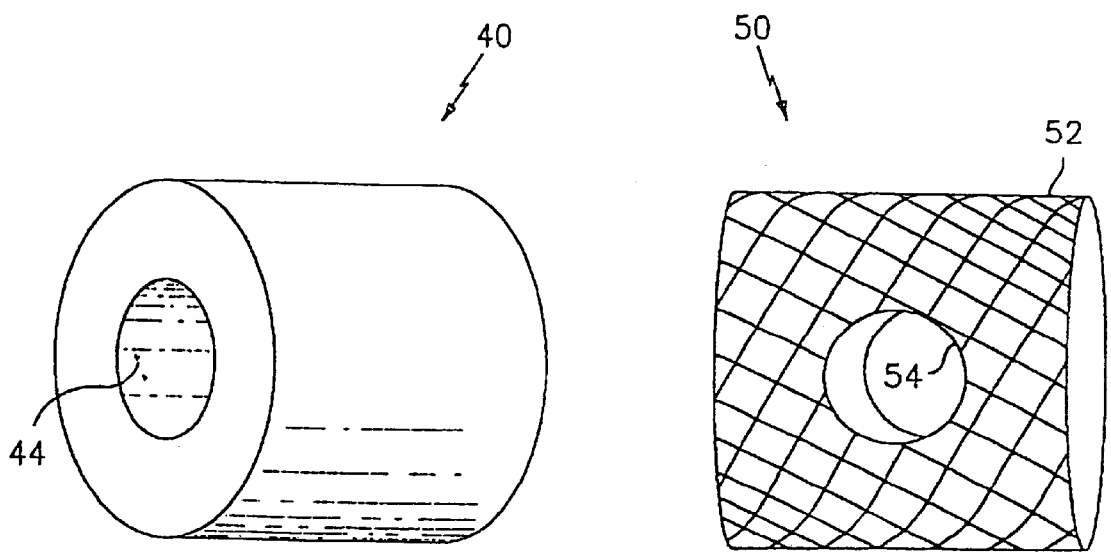
FIG. 5
FIG. 6

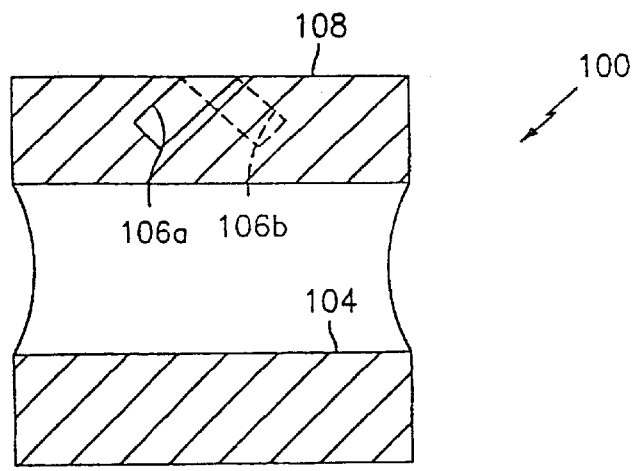
FIG. 12
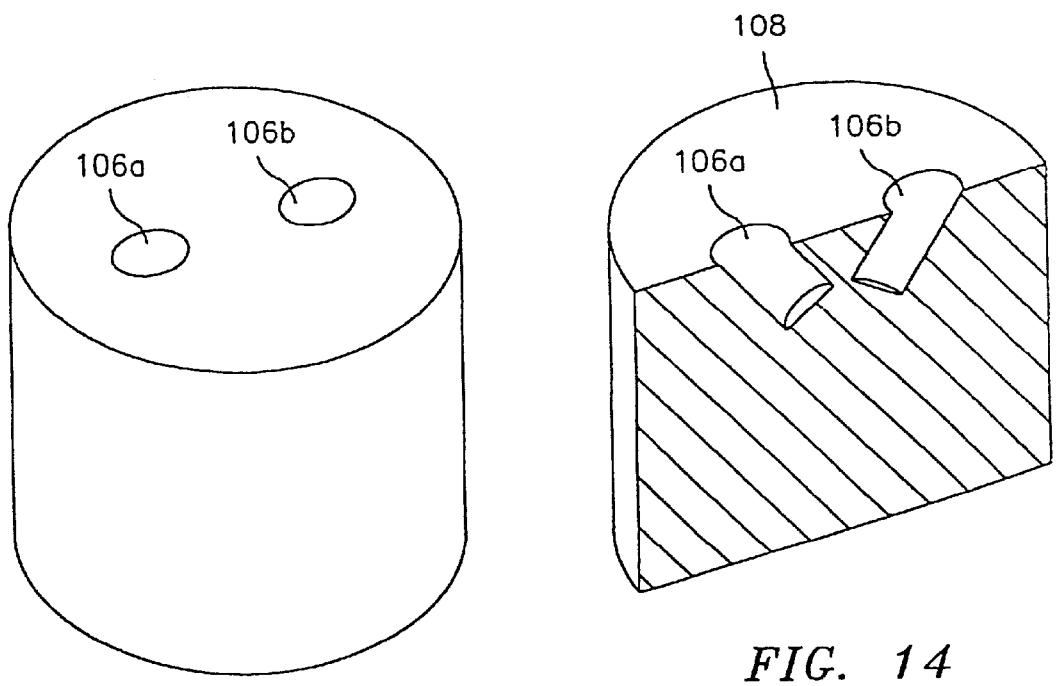
FIG. 13
FIG. 14

CERVICAL DOWEL AND INSERTION TOOL

This application claims priority from U.S. provisional application Ser. No. 60/158,074, filed Oct. 7, 1999, the entirety of which is incorporated herein by reference.

BACKGROUND

1. Technical Field

The present disclosure relates generally to surgical implants and to implant insertion tools and, more specifically, to cervical dowels and an insertion tool for inserting a cervical dowel into a receiving bed formed in an intervertebral space.

2. Background of Related Art

Cervical dowels and tools for inserting cervical dowels into the intervertebral space are well known in the prior art. For Example, U.S. Pat. No. 4,877,020 to Vich discloses a bone dowel and an instrument for inserting the bone dowel into the cervical region of the spine. The Vich dowel includes a cylindrical body, which is formed of bone extracted from the patient's iliac crest. A coil or thread is formed about the exterior surface of the dowel and the dowel is screwed into a previously prepared bed in the intervertebral space. Vich discloses a pair of instruments for inserting the dowel into the intervertebral space. A first instrument includes a pair of pins and a centrally located screw. The screw and pins penetrate one end of the dowel to secure the dowel onto a distal end of the insertion tool. Vich also discloses an insertion tool having an expandable sleeve portion which is positioned over one end of the dowel and clamped down to secure the dowel to the insertion tool.

Vich's insertion tools are lacking in several respects. For example, Vich's screw/pin insertion tool requires that the dowel be screwed onto the insertion tool. This makes it difficult and time consuming for a surgeon to disengage the dowel from the insertion tool. Moreover, Vich's expandable sleeve insertion tool has a diameter larger than diameter of the dowel. Thus, it is very difficult using this insertion tool to fully insert a dowel into the intervertebral space.

Accordingly, a continuing need exists for a dowel insertion tool which can be quickly and easily attached and detached to/from a bone dowel. Moreover, a continuing need exists for an insertion tool which does not interfere with dowel insertion into the intervertebral space.

SUMMARY

In accordance with the present disclosure, a dowel and a dowel insertion tool for inserting the dowel into the intervertebral space are provided. The implant insertion tool includes a T-shaped handle having a hollow sleeve which extends from the T-shaped handle. A shaft extends from the handle through the sleeve and includes a transverse extension. A rotatable knob having an annular channel positioned to receive the transverse extension is supported adjacent the handle. A pin is secured to the knob and extends into a helical camming channel formed in the sleeve.

Upon rotation of the knob, the pin moves within the camming channel to move the knob longitudinally about the sleeve. Movement of the knob effects longitudinal movement of the shaft. A plate is secured to the distal end of the shaft. A pair of prongs are slidably secured to the plate. Each of the prongs includes an enlarged head portion which is slidably positioned within a slot formed in the plate. A guide member is secured to the distal end of the sleeve. The guide member includes a pair of guide bores which direct the prongs away from the sleeve at an angle to the longitudinal axis of the sleeve. The prongs are dimensioned to be received in bores formed in the trailing end of a cervical dowel. Because the prongs engage the dowel at an angle, the dowel is both rotatably and longitudinally fixed to the insertion tool.

BRIEF DESCRIPTION OF THE DRAWINGS

Preferred embodiments of the presently disclosed dowel insertion tool and associated dowels are described herein with reference to the drawings, wherein:

FIG. 4 is a side elevational view of the cervical bone dowel shown in FIG. 3;

FIG. 5 is a perspective view of yet another embodiment of the presently disclosed cervical bone dowel;

FIG. 6 is a perspective view of yet another embodiment of the presently disclosed cervical bone dowel;

FIG. 12 is a side cross-sectional view of the cervical bone dowel shown in FIG. 9;

FIG. 13 is a perspective view of yet another embodiment of the presently disclosed cervical bone dowel;

FIG. 14 is a side cross-sectional view of the cervical bone dowel shown in FIG. 13;

DETAILED DESCRIPTION OF PREFERRED EMBODIMENTS

Figure 1:
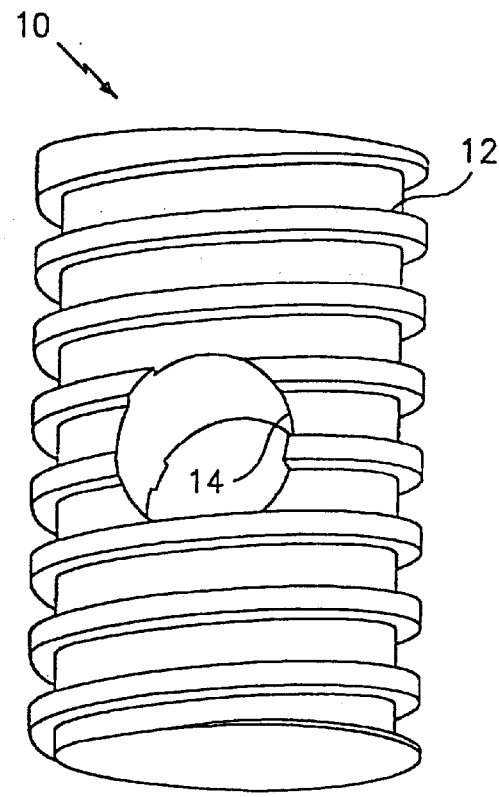
FIG. 1 is a perspective view of one embodiment of the presently disclosed cervical bone dowel.

Preferred embodiments of the presently disclosed cervical dowel and cervical dowel insertion tool will now be described in detail with reference to the drawings, wherein like reference numerals designate corresponding elements in each of the several views.

FIGS. 1–16 illustrate a plurality of different embodiments of bone dowels which are preferably configured and dimensioned to be received in the cervical spine. Alternatively, any one or all of these dowels may be dimensioned to be received in the other areas of the spine, e.g., the lumbar or thoracic spine.

Figure 2:
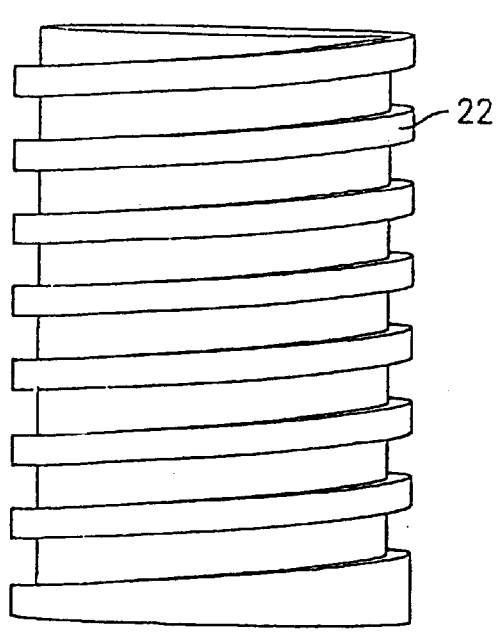
FIG. 2 is a side elevational view of another embodiment of the presently disclosed cervical bone dowel.

Referring to FIG. 1, cylindrical dowel 10 has a threaded body 12 defining a throughbore 14 which extends transversely to the longitudinal axis of the dowel. Preferably, dowel 10 is constructed from cortical and/or cancellous bone. Alternately, other biocompatible materials can be used including surgical grade steels, titanium, ceramic, etc. Throughbore 14 may be formed by a portion of the intramedullary canal of the bone from which the dowel has been cut, drilled into dowel 10 or, molded during formation of dowel 10. Alternately, as shown in FIG. 2, cylindrical dowel 20 having a threaded exterior 22 may not have a throughbore.

Figure 3:
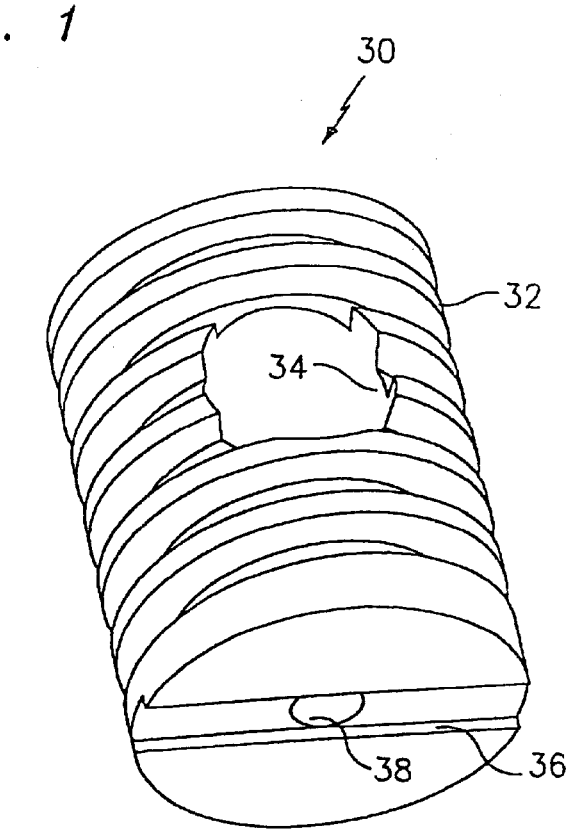
FIG. 3 is a perspective view of another embodiment of the presently disclosed cervical bone dowel.

FIGS. 3 and 4 illustrate a cylindrical dowel 30 including a threaded exterior 32, a transverse throughbore 34, and further including a slot 36 and tapped hole 38 formed in one end of the dowel. The slot 36 and the hole 38 are dimensioned and configured to engage a dowel insertion tool, not shown.

Referring to FIG. 5, a cylindrical dowel 40 including a throughbore 44 has a longitudinal axis which is parallel to the longitudinal axis of the dowel. FIG. 6 illustrates a cylindrical dowel 50 having a cross-hatched, knurled or roughened exterior surface 52 and a transverse throughbore 54. Surface 52 functions to retain dowel 50 in a fixed position after it has been inserted into a receiving bed formed in the intervertebral space.

Figure 7:
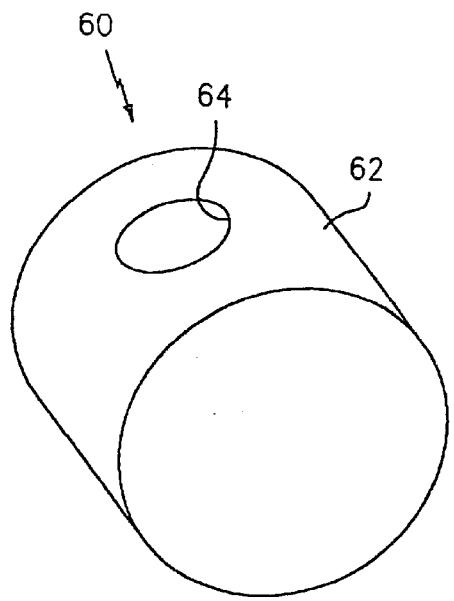
FIG. 7 is a perspective view of yet another embodiment of the presently disclosed cervical bone dowel.
Figure 8:
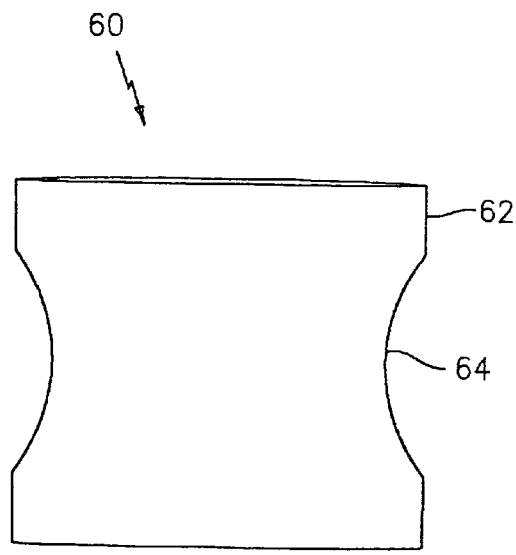
FIG. 8 is a side elevational view of the cervical bone dowel shown in FIG. 7.
Figure 9:
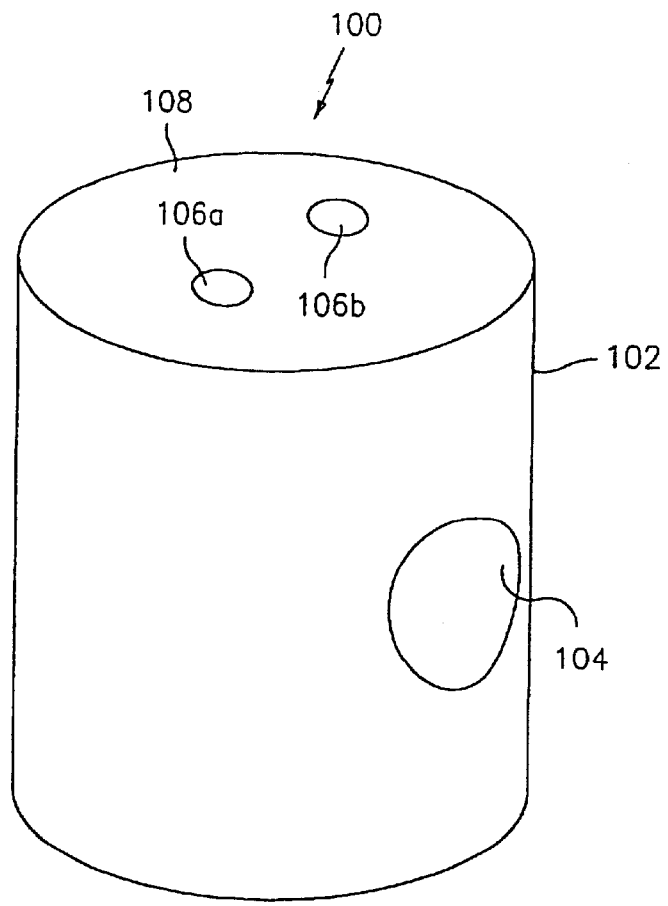
FIG. 9 is a perspective view of yet another embodiment of the presently disclosed cervical bone dowel.
Figure 10:
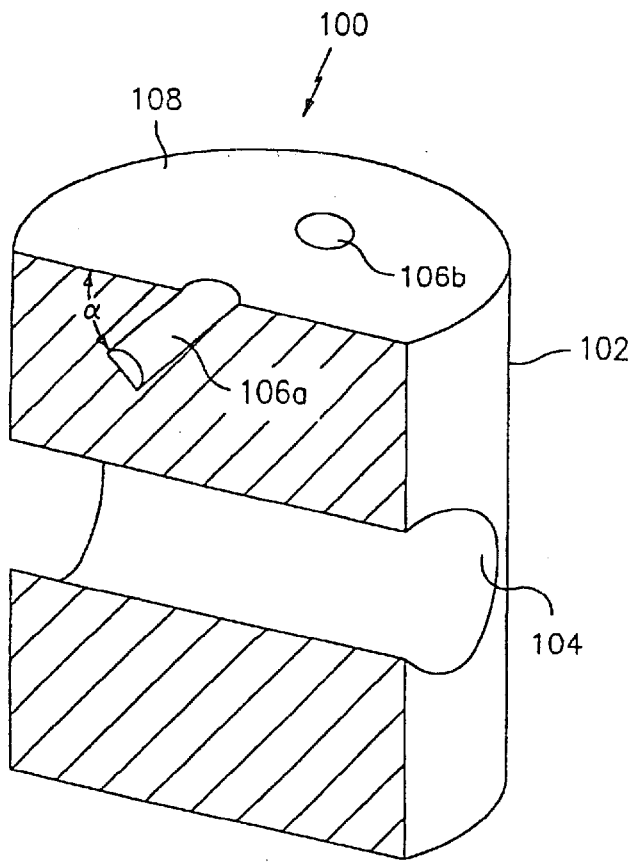
FIG. 10 is a side cross-sectional view of the cervical bone dowel shown in FIG. 9.
Figure 11:
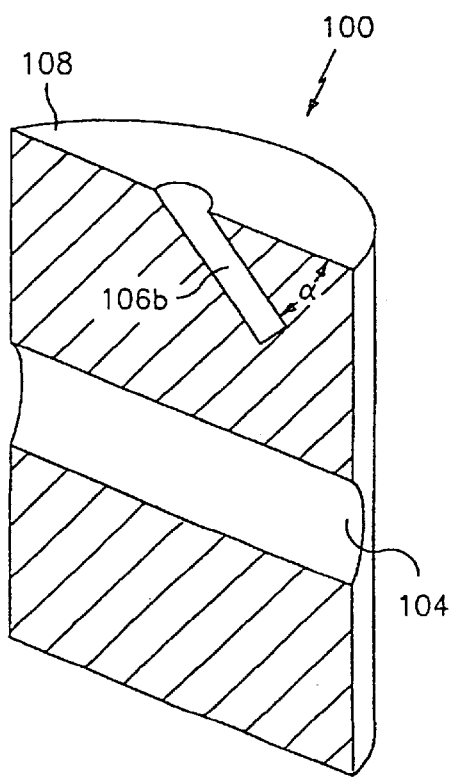
FIG. 11 is a side cross-sectional view of the cervical bone dowel shown in FIG. 9.

FIGS. 7 and 8 illustrate a cylindrical dowel 60 having a substantially smooth exterior surface 62 and a transverse throughbore 64.

FIGS. 9–16 illustrate a cylindrical dowel 100 having a substantially smooth exterior surface 102, a transverse throughbore 104 and a pair of insertion tool engaging bores 106a and 106b. Insertion tool engaging bores 106a and 106b are formed in one end surface 108 of dowel 100. Alternatively, the exterior surface of dowel 100 can be threaded or roughened to provide a retaining surface.

Figure 15:
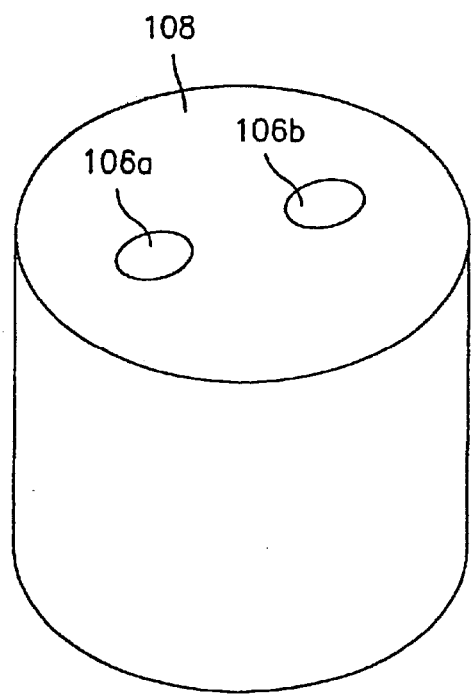
FIG. 15 is a perspective view of yet another embodiment of the presently disclosed cervical bone dowel.
Figure 16:
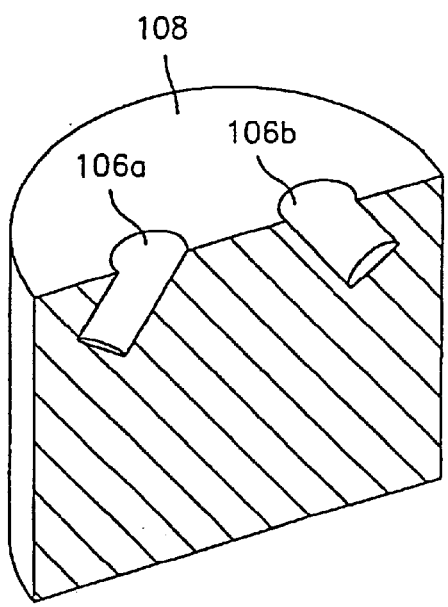
FIG. 16 is a side cross-sectional view of the cervical bone dowel shown in FIG. 15.
Figure 17:
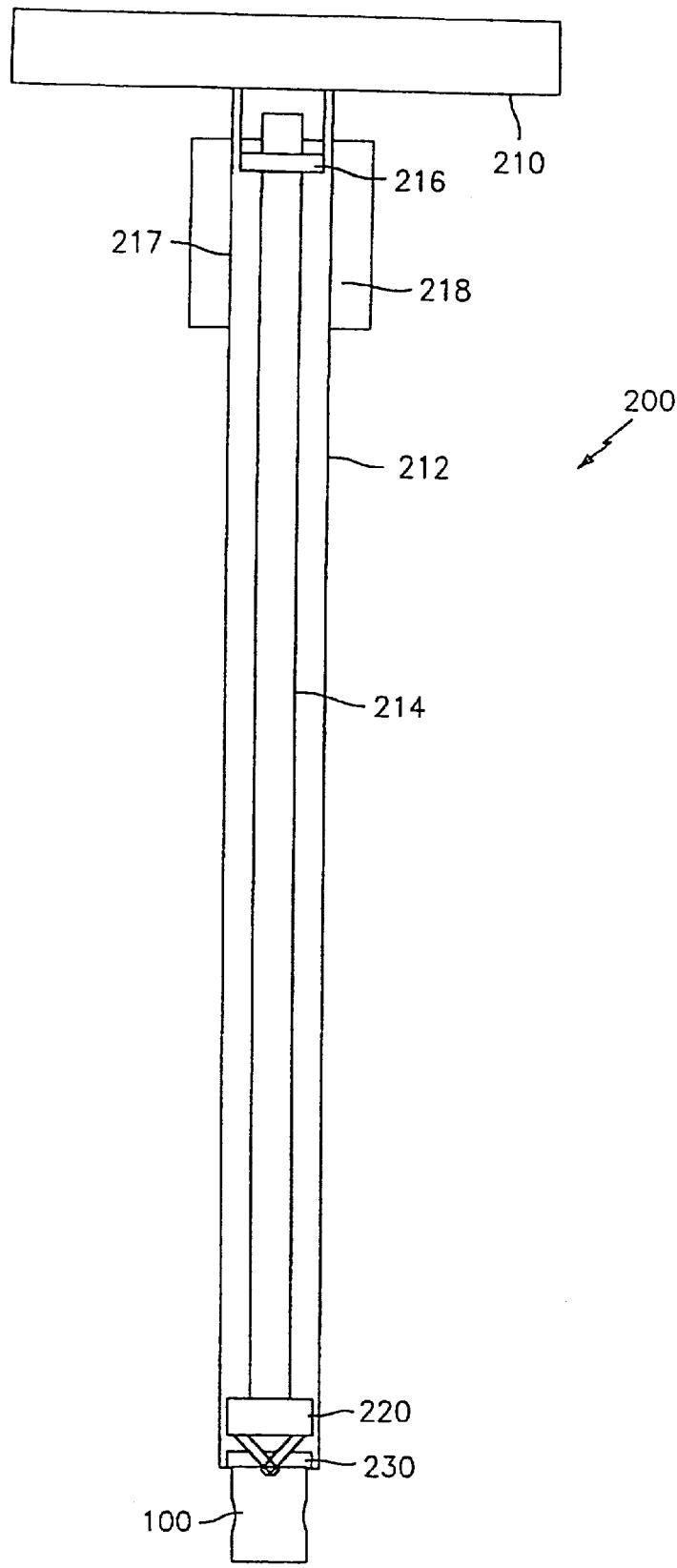
FIG. 17 is a side elevational view of one embodiment of the presently disclosed dowel insertion tool with a bone dowel secured to a distal end thereof.
Figure 18:
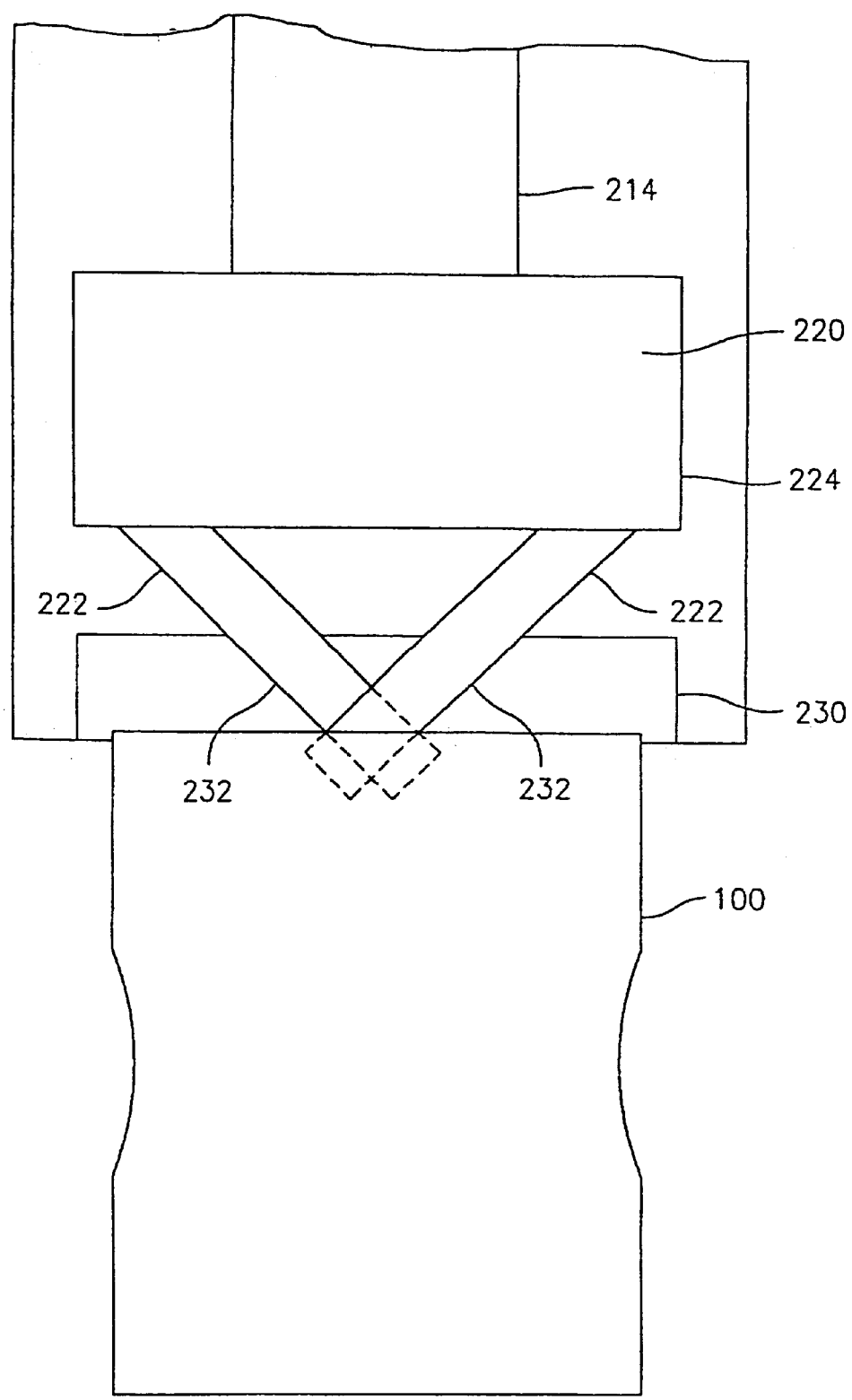
FIG. 18 is an enlarged partial cutaway view of the distal end of the insertion tool shown in FIG.17.
Figure 19:
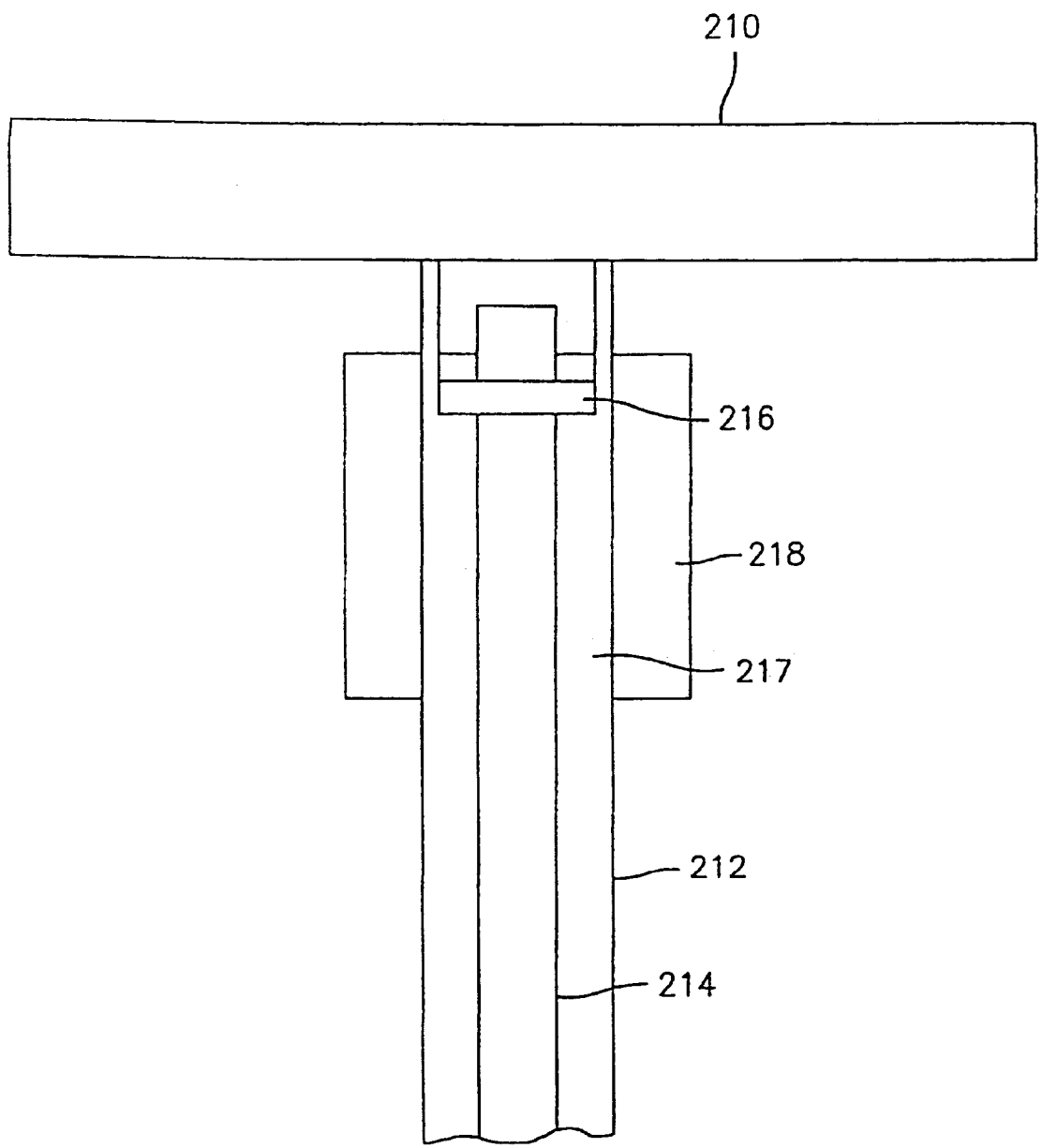
FIG. 19 is an enlarged partial cutaway view of the proximal end of the insertion instrument shown in FIG. 1.
Figure 22:
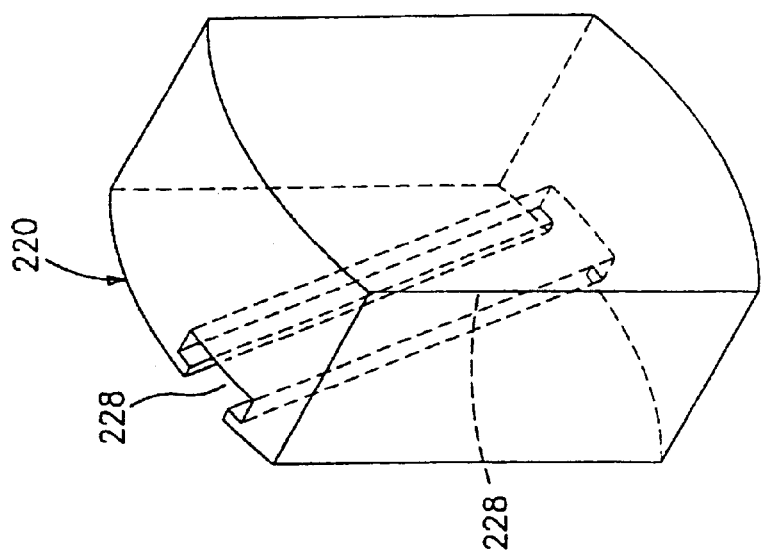
FIG. 22 is yet another perspective from the front end of the prong support plate of the insertion tool shown in FIG. 17.
Figure 21:
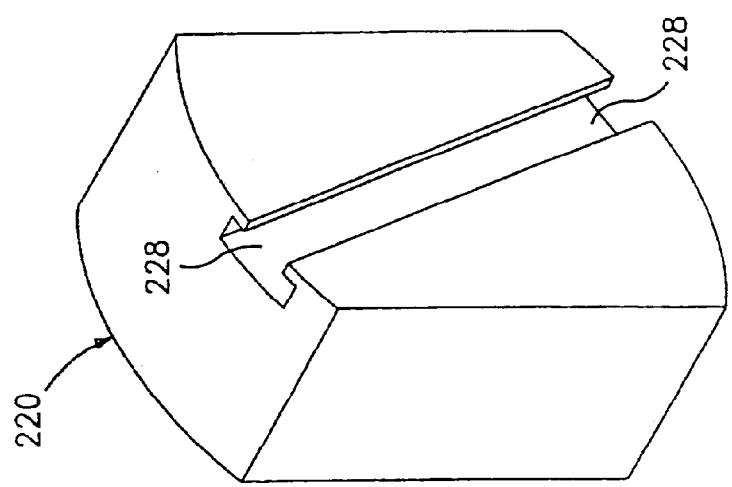
FIG. 21 is another perspective view from the front end of the prong support plate of the insertion tool shown in FIG. 17.
Figure 20:
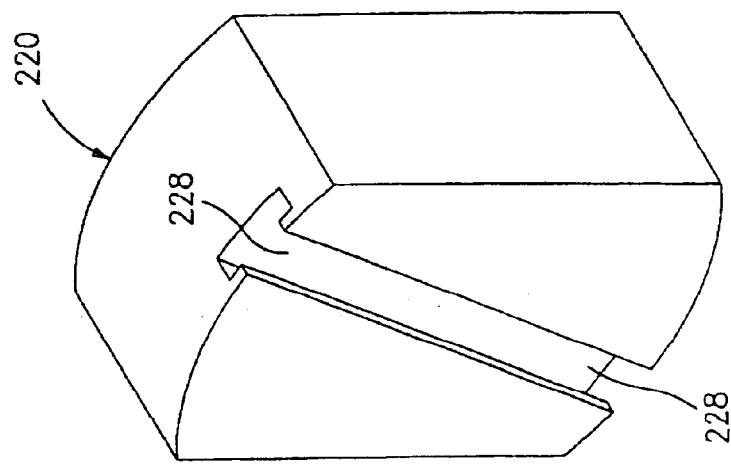
FIG. 20 is a perspective view from the front end of the prong support plate of the insertion tool shown in FIG. 17.
Figure 23:
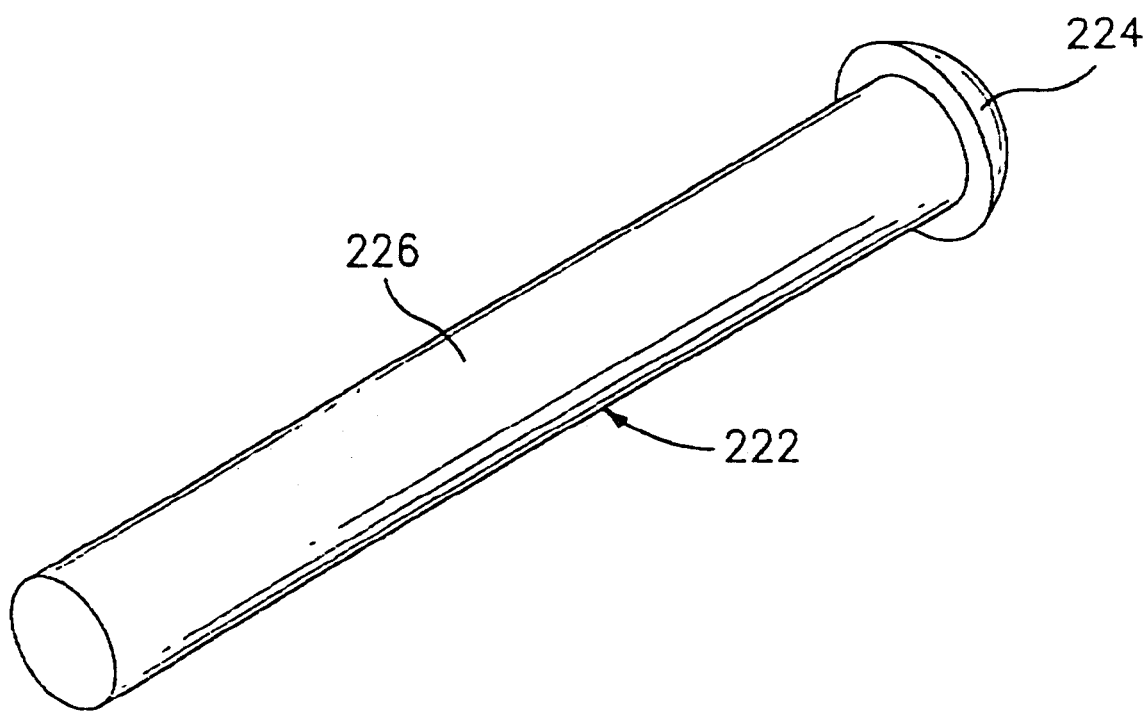
FIG. 23 is a perspective view of a prong of the insertion tool shown in FIG. 17.

As illustrated in FIGS. 9–12, engaging bores 106, diverge outwardly from each other in spaced vertical planes and form an angle α of approximately 45° with respect to a plane defined by end surface 108 of dowel 100. Alternately, the direction, location and angle of the engaging bores 106a and 106b may vary so long as they are capable of receiving insertion tool prongs described below. For example, engaging bores 106a and 106b may converge toward each other in a common vertical plane (FIGS. 13 and 14) or bores 106a and 106b may diverge from each other in a common vertical plane (FIGS. 15 and 16). Moreover, the angle of bores 106 may vary substantially from that illustrated. For example, the angle of bores 106 with respect to the plane defined by end surface 108 of dowel 100 may be approximately 15°, 75°, 60° etc.

FIGS. 17–20 illustrate an insertion tool 200 for engaging and releasably securing dowel 100 to a distal end thereof. Briefly, insertion tool 200 includes a T-handle 210 having a hollow sleeve 212 extending therefrom. A shaft 214 extends from a proximal end of sleeve 212 to the distal end of sleeve 212. The proximal end of shaft 214 has a transverse extension 216. A rotatable knob 218 includes an annular channel (not shown) formed on its internal surface. Knob 218 is positioned about shaft 214 such that transverse extension 216 is positioned in the annular channel. A pin 217 is secured to knob 218 and extends into a camming channel (not shown), e.g., helical channel, formed in sleeve 212. Upon rotation of knob 218, pin 217 moves within the camming channel formed in sleeve 212 to move knob 218 longitudinally about sleeve 212. Movement of knob 212 causes corresponding longitudinal movement of shaft 214. A plate 220 is secured to the distal end of shaft 214. A pair of prongs 222 are slidably secured to plate 220. Each of the prongs 222 includes an enlarged head portion 224 and an elongated body portion 226. Each head portion 224 is slidably positioned within a respective slot 228 formed in plate 220. A guide member 230 is secured to the distal end of sleeve 212. Guide member 230 includes a pair of guide bores 232 which guide and direct prongs 222 at an angle to the 20 longitudinal axis guide sleeve 1212 into bores 106 of dowel 100.

Figure 24:
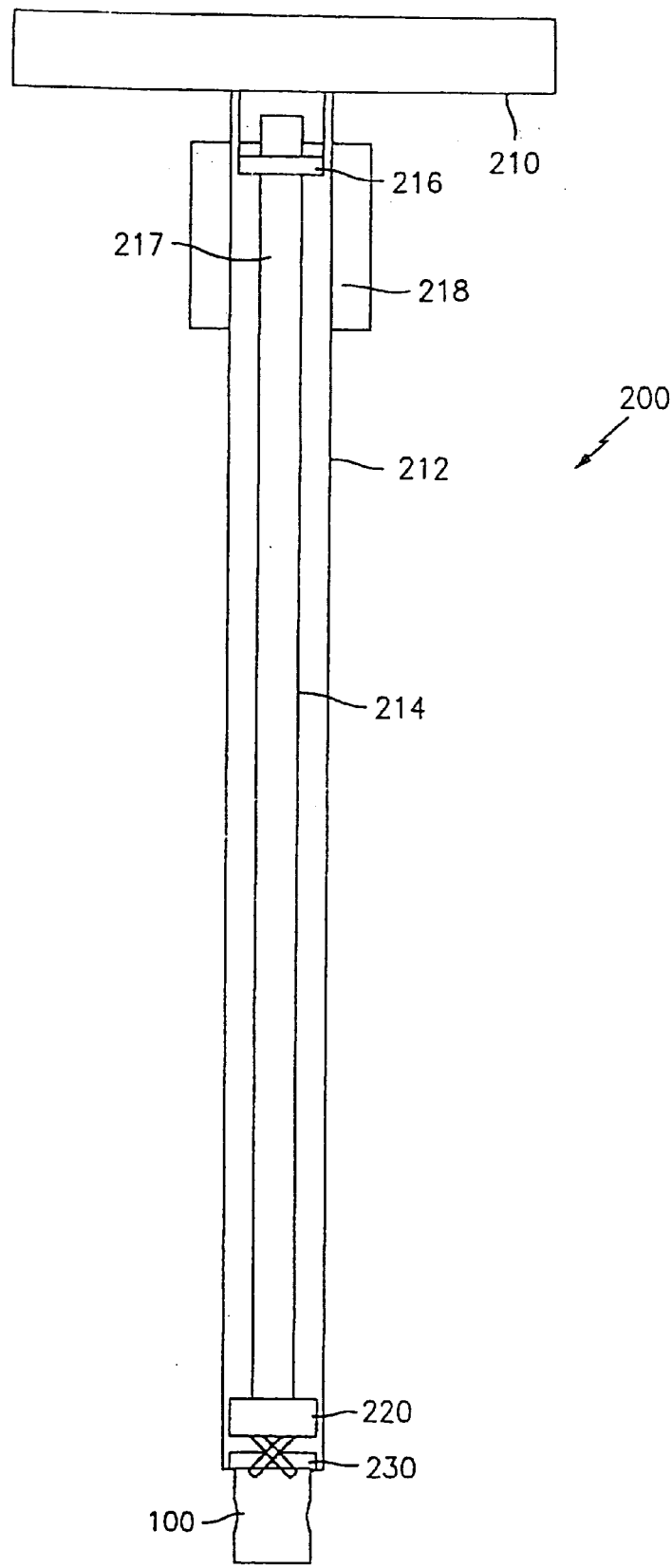
FIG. 24 is a side elevational view of the dowel insertion tool shown in FIG. 17 with the prongs in a partially advanced state.
Figure 25:
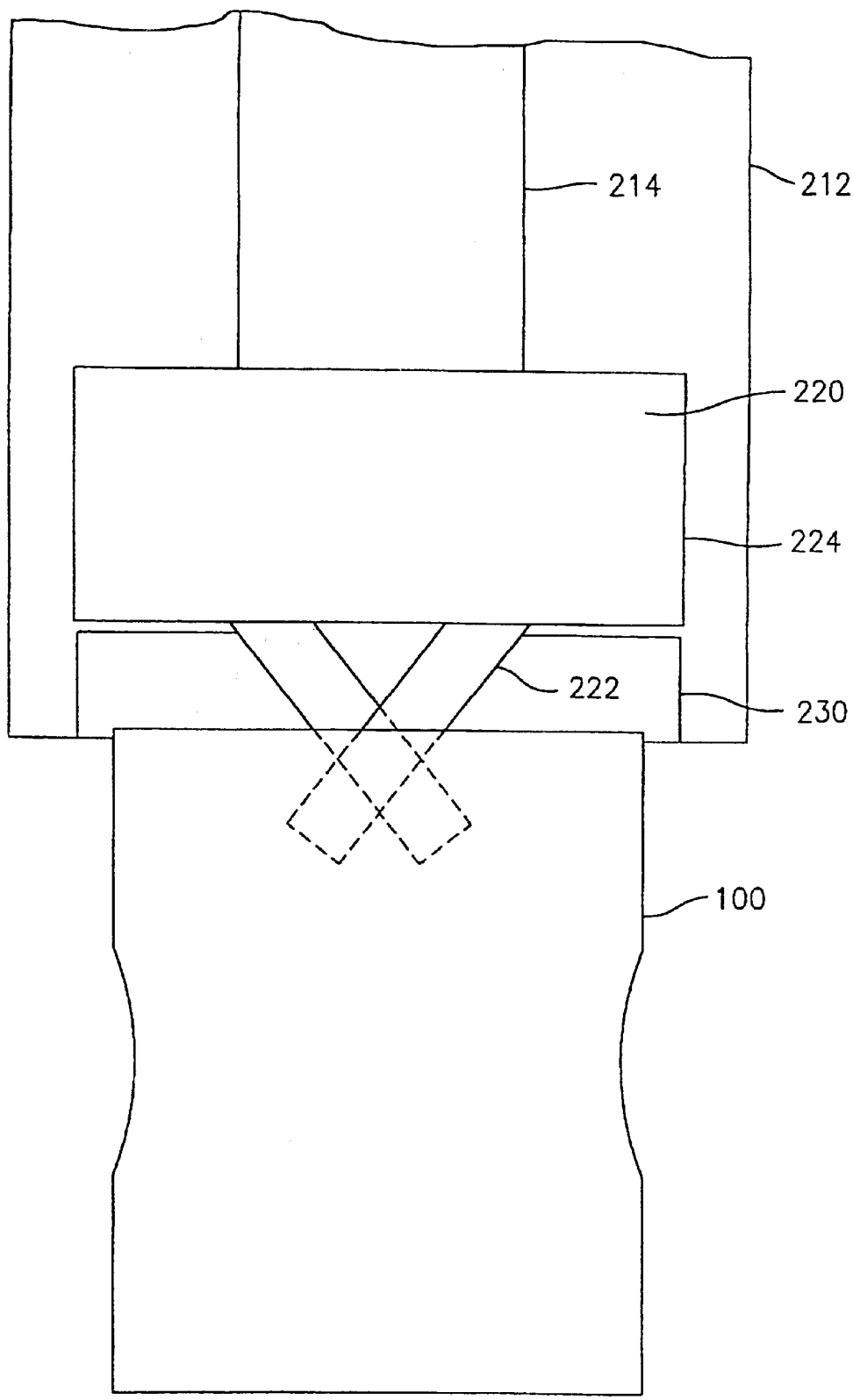
FIG. 25 is an enlarged view of the dowel insertion tool shown in FIG. 17 in an advanced state.

Referring to FIGS. 24 and 25, in use, a dowel 100 is positioned adjacent the distal end of sleeve 212 and knob 218 is rotated to advance shaft 214 within sleeve 212. As shaft 214 is advanced, plate 220 is advanced towards guide member 230 to advance prongs 222 through guide bores 232 and into engaging bores 106a and 106b of dowel 100. Because the angle of guide bores 232 and engaging bores 106a and 106b are fixed, each head portion 224 is forced to slide within a respective slot 228 of plate 220 as plate 220 approaches guide member 230. Because the insertion prongs 222 extend at a fixed angle through dowel 100, dowel 100 is both rotatably and longitudinally fixed with respect to the distal end of insertion tool 200. Thus, tool 200 can be rotated to apply a torque to dowel 100 or pushed/pulled to move dowel 100 longitudinally.

Figure 26:
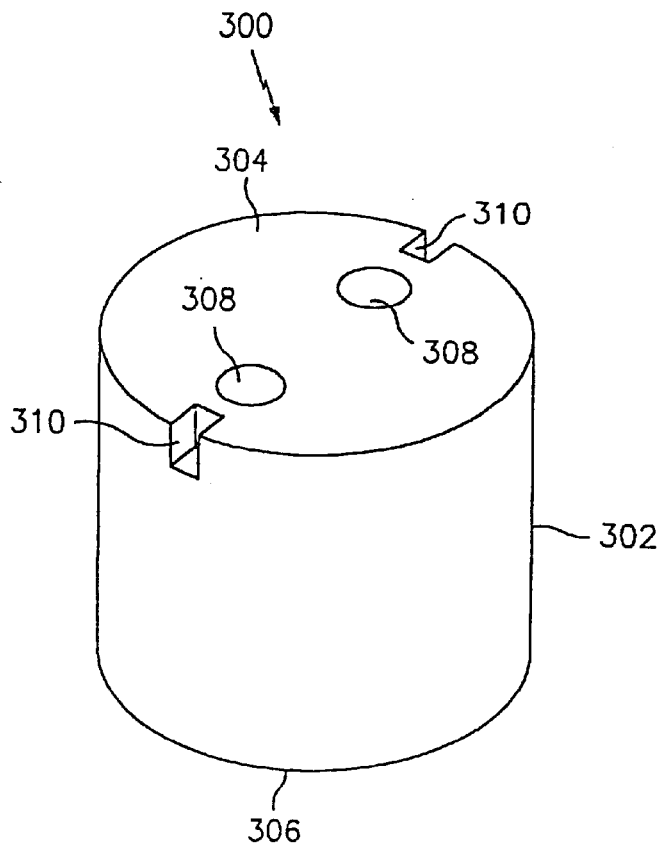
FIG. 26 is a perspective view of yet another embodiment of the presently disclosed cervical bone dowel.
Figure 27:
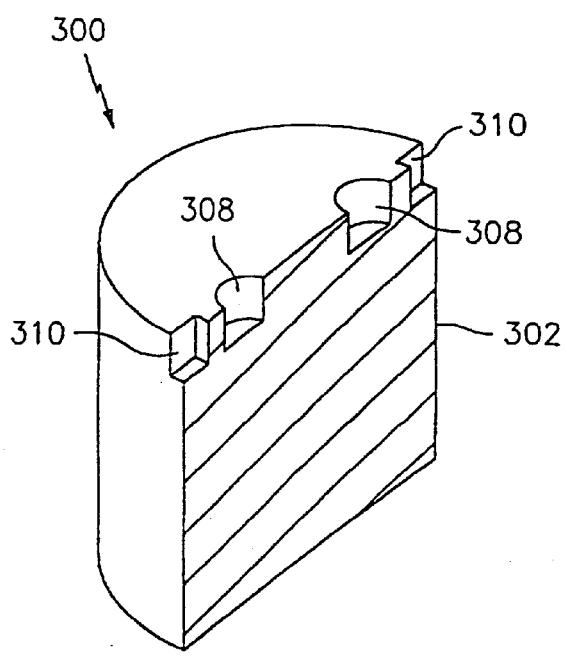
FIG. 27 is a perspective, cross-sectional view of the cervical bone dowel shown in FIG. 26.

FIGS. 26 and 27 illustrate an alternate embodiment of the intervertebral dowel shown generally as 300. Dowel 300 includes a cylindrical body 302 having a first end face 304 and a second end face 306. A pair of holes 308 are formed in first end face 304 at locations spaced from the central axis of dowel 300. A pair of slots 310 are formed in the outer periphery of first end face 304. Slots 310 are positioned such that they extend along a portion of the outer cylindrical surface of dowel 300. Holes 306 are dimensioned and configured to receive insertion tool prongs to facilitate torquing of the dowel. Slots 310 are configured and dimensioned to receive clamping arms of a clamping mechanism (not shown) to secure dowel 300 to an insertion tool (not shown).

Figure 28:
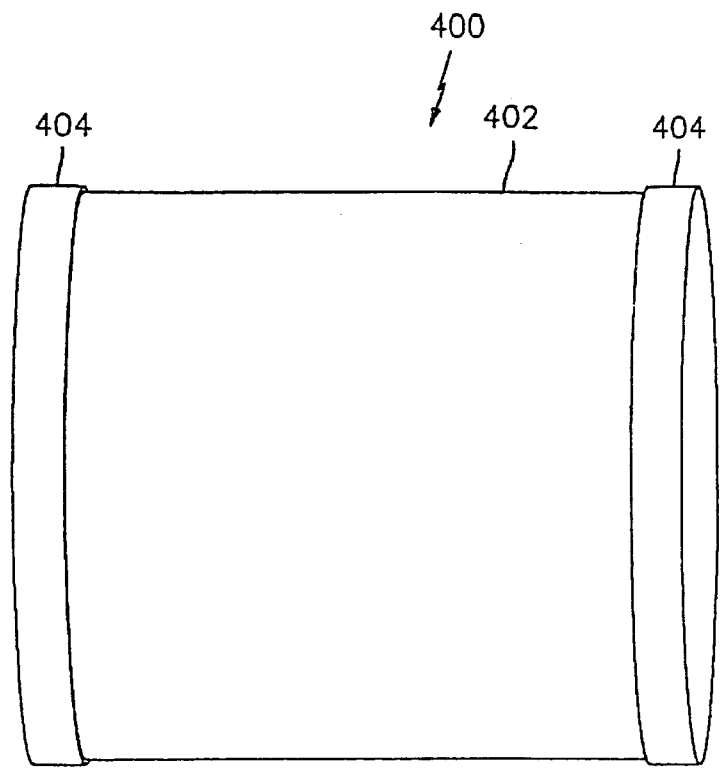
FIG. 28 is a perspective view of yet another embodiment of the presently disclosed cervical bone dowel.
Figure 29:
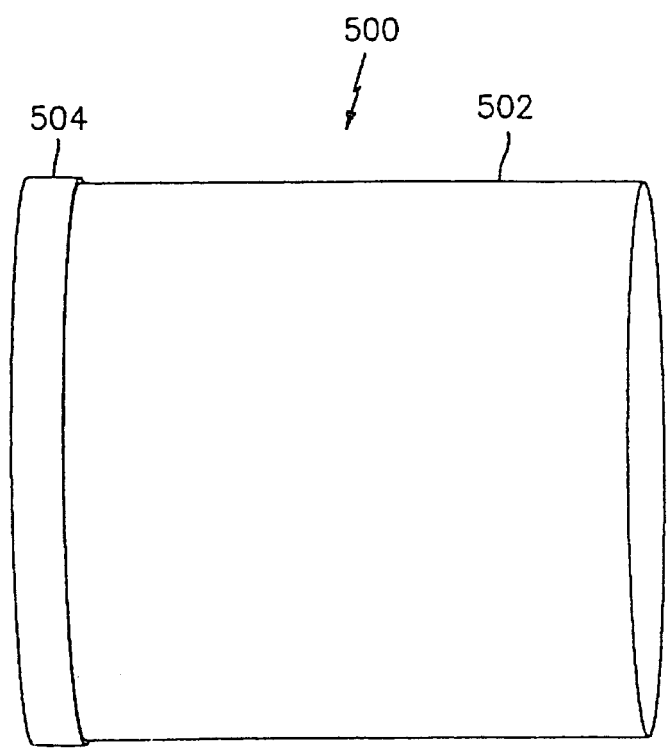
FIG. 29 is yet another embodiment of the presently disclosed cervical bone dowel

FIGS. 28 and 29 illustrate other alternate embodiments of the intervertebral dowel shown generally as 400 (FIG. 28) and 500. Dowel 400 includes a cylindrical body portion 402 formed from cancellous bone and opposite end portion 404 formed from cortical bone. Dowel 500 includes a cylindrical body portion 502 formed from cancellous bone and a single end portion 504 formed from cortical bone. Alternately, the entire dowel may be formed from cortical or cancellous bone.

It will be understood that various modifications may be made to the embodiments disclosed herein. For example, the particular angle of the prongs may vary. Moreover, the dowels may be formed from a variety of biocompatible materials. Therefore, the above description should not be construed as limiting, but merely as exemplifications of preferred embodiments. Those skilled in the art will envision other modifications within the scope and spirit of the claims appended hereto.

What is claimed:

1. An intervertebral dowel comprising:
    a cylindrical body formed from bone, the cylindrical body defining a longitudinal axis and having a first end, a second end and cylindrical sidewall;
    a single throughbore formed transversely through the cylindrical sidewall; and
    at least one insertion tool engaging bore formed in the first end of the cylindrical body, the at least one insertion tool engaging bore having a longitudinal axis which is oblique to the longitudinal axis of the cylindrical body.

2. An intervertebral dowel according to claim 1, wherein the throughbore is formed by an intramedullary canal of the bone from which the dowel has been cut.

3. An intervertebral dowel according to claim 1, wherein the dowel is formed from cancellous bone.

4. An intervertebral dowel according to claim 1, wherein the dowel is formed from cortical bone.

5. An intervertebral dowel according to claim 1, wherein the at least one insertion tool engaging bore includes a plurality of bores.

6. An intervertebral dowel according to claim 1, wherein the cylindrical sidewall of the dowel includes a helical thread.

7. An intervertebral dowel according to claim 1, wherein the cylindrical sidewall of the dowel includes a roughened surface.

8. An intervertebral dowel according to claim 1, wherein the at least one insertion tool engaging bore includes a pair of bores angled in a diverging direction to each other.

9. An intervertebral dowel according to claim 1, wherein the at least one insertion tool engaging bore includes a pair of bores angled in a converging direction to each other.

* * * * *